(12) United States Patent
Sukkau

(10) Patent No.: US 11,442,126 B2
(45) Date of Patent: Sep. 13, 2022

(54) SYSTEM AND METHOD FOR ESTIMATING A RELATIVE SUBSTANCE COMPOSITION OF A PORTION OF A BODY OF A PATIENT

(71) Applicant: Siemens Healthcare GmbH, Erlangen (DE)

(72) Inventor: Johann Sukkau, Herzogenaurach (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/120,100

(22) Filed: Dec. 11, 2020

(65) Prior Publication Data

US 2021/0181284 A1 Jun. 17, 2021

(30) Foreign Application Priority Data

Dec. 13, 2019 (EP) .................................. 19215964.8

(51) Int. Cl.
*G01V 3/00* (2006.01)
*G01R 33/48* (2006.01)
(Continued)

(52) U.S. Cl.
CPC ....... *G01R 33/4828* (2013.01); *G01R 33/543* (2013.01); *G06N 3/04* (2013.01); *G06N 3/08* (2013.01); *G16H 10/60* (2018.01)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS

| 2004/0152952 A1* | 8/2004 | Gotlib | G16H 40/67 |
| | | | 600/300 |
| 2012/0041778 A1* | 2/2012 | Kraft | G16Z 99/00 |
| | | | 705/2 |

(Continued)

FOREIGN PATENT DOCUMENTS

| CN | 104502873 A | * 4/2015 |
| CN | 106324011 B | * 10/2017 |

(Continued)

OTHER PUBLICATIONS

European Search Report for European Application No. 19215964.8—1010 dated Jun. 4, 2020.

*Primary Examiner* — Walter L Lindsay, Jr.
*Assistant Examiner* — Frederick Wenderoth
(74) *Attorney, Agent, or Firm* — Lempia Summerfield Katz LLC

(57) ABSTRACT

A relative substance composition (RSC) of a portion of a body of a patient in a field of view for a medical image to be taken from the patient in a medical imaging scan is estimated. An input interface receives a piece of patient information data (PPID) and receives a piece of field-of-view information data (PFID). A computing device is configured to implement a trained machine learning algorithm (MLA). The trained MLA is configured and trained to receive the PPID and the PFID received by the input interface as an input and to generate as an output an output signal indicating an RSC of a portion of the body of the patient for the medical image based on the PPID and the PFID. An output interface outputs at least the output signal.

16 Claims, 5 Drawing Sheets

(51) Int. Cl.
*G16H 10/60* (2018.01)
*G01R 33/54* (2006.01)
*G06N 3/04* (2006.01)
*G06N 3/08* (2006.01)

(58) Field of Classification Search
USPC .......................................................... 324/309
See application file for complete search history.

(56) References Cited

U.S. PATENT DOCUMENTS

| | | |
|---|---|---|
| 2013/0249552 A1 | 9/2013 | Imamura |
| 2013/0282078 A1* | 10/2013 | Wacnik .............. A61N 1/36071 607/59 |
| 2015/0077115 A1 | 3/2015 | Fautz |
| 2015/0168521 A1 | 6/2015 | Ozawa |
| 2015/0285883 A1 | 10/2015 | Clark |
| 2017/0105700 A1* | 4/2017 | Bar-Zion ................ A61B 8/065 |
| 2018/0197624 A1* | 7/2018 | Robaina .................. G06F 3/013 |
| 2021/0088613 A1 | 3/2021 | Ruyters et al. |

FOREIGN PATENT DOCUMENTS

| | | | |
|---|---|---|---|
| CN | 107392897 A | * | 11/2017 |
| CN | 108742623 A | * | 11/2018 |
| EP | 3796026 A1 | | 3/2021 |
| WO | 2014082128 A1 | | 6/2014 |

* cited by examiner

SYSTEM AND METHOD FOR ESTIMATING A RELATIVE SUBSTANCE COMPOSITION OF A PORTION OF A BODY OF A PATIENT

This application claims the benefit of European Patent Application No. EP 19215964.8, filed Dec. 13, 2019, which is hereby incorporated by reference in its entirety.

BACKGROUND

The present embodiments relate to estimating a relative substance composition of a portion of a body of a patient, training a machine learning algorithm for such estimating, and generating training data for such training.

In magnetic resonance (MR) scans (e.g., image acquisitions), nuclear spins of hydrogen atoms are resonantly excited by radio frequency pulses. A resonance frequency of each spin is proportional to a magnetic field B0 at a location of a nucleus of the hydrogen atoms. Therefore, the terms "frequency" and "B0" are sometimes used as synonyms.

In any MR scan, the local B0 field may vary for a number of reasons. For example, the magnetic field strength may drift (e.g., due to temperature changes in the magnet cooling shields that may lead to global frequency shifts). Also, the susceptibility of biological matter in the body of the patient body and corresponding boundaries may lead to local frequency shifts, generally addressed by shimming. Shimming is a process by which the main magnetic field is made more homogeneous.

A shimming method is described, for example, in US 2015/00771155 A1, in which it is proposed to acquire magnetic resonance data by measurements implemented at two different echo times. A difference of the two different echo times forms a dephasing time after an excitation at at least two different dephasing times.

Microscopic frequency shifts may also be caused as a result of the chemical bonds of the hydrogen atom (e.g., in fat or water molecules). The chemical shifts are usually determined in parts per million (ppm), as the chemical shifts depend on the magnetic field strength applied.

In order to achieve best possible contrast and signal-to-noise-ratio (SNR), and to successfully employ techniques such as fat or water saturation, the resonance frequencies of the hydrogen atoms within the field of view of each MR scan are be precisely known and used for setting an MR device up for a scan. Therefore, usually a frequency adjustment measurement is conducted for each MR scan using a specialized sequence. The result is a spectrum of signal intensities per frequency inside the field of view of the MR scanning device. These spectra may be designated as resonance frequency spectra (RFS) that typically show distinct peaks generated by resonance frequency maxima of different substances (e.g., water, fat, silicone, . . . ) within a body of a patient.

These resonance frequency spectra usually include peaks that correspond to resonance frequency maxima for different substances such as fat or water. FIG. 7 shows a schematic resonance frequency spectrum 1 with a distinct peak 2 for the resonance frequency of fat (e.g., body fat) and a distinct second peak 3 for the resonance frequency of water. The horizontal axis shows frequency values as deviations from a currently set frequency value for the resonance frequency of water, and the vertical axis shows signal strength in arbitrary units. Current algorithms essentially determine the peaks (e.g., for water, dashed line) by adjusting Lorentzian functions to the resonance frequency spectrum (RFS) and use an optimization to create a best fit. In this way, a fitting curve 4 for a resonance frequency spectrum (RFS) as shown in FIG. 7 is usually generated automatically.

However, in other cases, as illustrated in FIG. 8, the measured resonance frequency spectrum 5 may be more complicated so that the fitting curve 6 generated by the prior art algorithms often fails to capture the details of the resonance frequency spectrum (RFS).

In each resonance frequency spectrum (RFS), at least the "water peak" (e.g., the peak resulting from the resonance frequency of hydrogen atoms bound in water molecules) is to be identified. Automated systems, however, are struggling to identify the correct peaks within such RFS with the corresponding substance as relative positions and heights vary (e.g., due to the different substance composition ratios (SCRs) within each particular body and the field of view chosen for a specific scan thereof). If two peaks are confused (e.g., the "fat peak", the peak resulting from the resonance frequency of hydrogen atoms bound in fat molecules, is confused for the "water peak"), the water resonance frequency setting of the MR device may be mistaken by 3.4 ppm. As a result, fat suppression in the MR scan may fail.

For example, in a field of view of a stomach of an obese patient, the substance composition ratio may indicate a high percentage of fat and a low percentage of water (e.g., adding up to 100%) so that the highest peak in the RFS will be the "fat peak". For another patient and/or another field of view, the highest peak may be, as is usually the case, the "water peak", as water is generally the dominant substance in the bodies of mammals.

One important piece of information for identifying peaks in the resonance frequency spectra (RFS) correctly is therefore information about the relative substance composition (RSC) of a body of a patient in the field-of-view of a specific scan.

The information about the relative substance composition (RSC) may also be used, or even be necessary, for certain shimming procedures.

SUMMARY AND DESCRIPTION

The scope of the present invention is defined solely by the appended claims and is not affected to any degree by the statements within this summary.

The present embodiments may obviate one or more of the drawbacks or limitations in the related art. For example, improved systems and methods for estimating a relative substance composition of a portion of a body of a patient with respect to, for example, a more accurate and more precise estimation are provided.

According to a first aspect of the present embodiments, a system is provided for estimating or determining a relative substance composition (RSC) of a portion of a body of a patient in a field of view for a medical image to be taken from the patient in a medical imaging scan. The system includes an input interface for receiving at least one piece of patient information data (PPID), and for receiving at least one piece of field-of-view information data (PFID). The system also includes a computing device configured to implement a trained machine learning algorithm (MLA), where the trained MLA is configured and trained to receive the at least one PPID and the at least one PFID received by the input interface as an input and to generate as an output at least one output signal indicating a relative substance composition (RSC) of a portion of the body of the patient for the medical image based on the at least one PPID and the at least one PFID. The system includes an output interface for outputting at least the at least one output signal.

For example, the medical imaging scan may be a magnetic resonance (MR) scan (e.g., magnetic resonance imaging (MRI)). However, other medical imaging techniques may also be employed for the medical imaging scan, such as computed tomography (CT), positron emission tomography (PET), and/or the like.

Instead of a fixed algorithm, a machine learning algorithm (MLA) is employed to generate the set of parameters of the relative substance composition (RSC) that has the advantage that the MLA may be continuously improved and updated.

Using the PPID and the PFID enables the MLA, to determine the RSC especially accurately and precisely.

The at least one PPID and/or the at least one PFID may be realized as, for example, one or more (e.g., two or more) input vector for the MLA, where each entry of the respective vector indicates a particular property of the patient or the field of view, respectively. Whenever herein a "vector" (e.g., a one-dimensional array) is mentioned, this may equally refer to a matrix (e.g., a two-dimensional array) or a tensor (e.g., a three- or more-dimensional array), since any matrix or tensor may easily be "unfolded" (e.g., reshaped into a vector structure). The input vector may, for example, be used as an input vector for an ANN as one type of MLA, where each entry of the input vector will be fed to one of the input nodes of the ANN.

The patient information data relates to (e.g., indicate or describe) the patient of which the medical image is to be taken with the field of view, and the field-of-view information relates to (e.g., indicates or describes) the field of view with which the medical image is to be taken of the patient. For example, the field of view may be understood to be a cuboid, the size of which is set within the B0 homogeneity area (e.g., to image a particular organ).

The input interface and/or the output interface may be realized in hardware and/or software. The input interface and/or the output interface may each include one or more different communication channels using one or more different communication protocols (e.g., HTTP). Each of the input interface and/or the output interface may be configured to connect to a cable-bound data connection and/or to a wireless data connection such as Bluetooth, Zigbee, WiFi, etc. The input interface and/or the output interface may also be configured to connect to Ethernet networks.

The computing device may be realized as any device, or any means, for computing. For example, the computing device may include at least one data processing unit (e.g., a calculating unit) such as at least one central processing unit (CPU), and/or at least one graphics processing unit (GPU), and/or at least one field-programmable gate array (FPGA), and/or at least one application-specific integrated circuit (ASIC), and/or any combination of the foregoing. The computing device may include a working memory operatively coupled to the at least one processing unit and/or a non-transitory memory operatively connected to the at least one processing unit and/or the working memory.

The computing device may be partially or completely realized as a remote device (e.g., as a cloud computing platform).

In some embodiments, refinements, or variants of embodiments, the relative substance composition (RSC) includes or consists of a ratio between water and fat. In one embodiment, the relative substance composition (RSC) includes or consists of a ratio between water, fat, and at least one substance not naturally occurring in the human body (e.g., silicone). Other substances not naturally occurring in the human body may be surgical steel or any other substance from which a prosthesis for the human body may be fabricated.

In one embodiment, the relative substance composition (RSC) consists of (e.g., describes or indicates) the relative percentages of water, fat, and silicone of the portion of the body of the patient in the field of view for the medical image to be taken. Silicone is a substance frequently used for aesthetic or prosthetic reasons in the human body (e.g., as part of implants such as in a female breast or in a buttock).

The presence of non-naturally occurring substances such as silicone is often not evident even to a human operator, and thus, in the prior art, the presence of such substances may have confused a human operator to some degree when interpreting resonance frequency spectra (RFS) in order to identify the peaks therein.

However, according to the present embodiments, the machine learning algorithm (MLA) is trained to accurately estimate (e.g., determine) the relative substance composition (RSC), which may include a percentage for silicone, and to output the RSC in the output signal. In this case, in which the relative substance composition (RSC) includes, consists of, or refers to water, fat and silicone, at least one piece of the at least one PPID indicates information about implants in the body of the patient (e.g., about amount, location and/or composition, such as substance used) of any implants.

For example, the at least one PPID may include information for each of the most common locations for silicone implants (e.g., left breast, right breast, left buttock, right buttock, and/or the like) about whether or not a silicone implant is located therein for the present patient. In an input vector, for example, each of the most common locations may be assigned one particular entry of the input vector, and a "0" may indicate the absence of a silicone implant in the location, whereas a "1" may indicate the presence of a silicone implant in the location. During training, the machine learning algorithm (MLA) will have learned that for fields of view that include such a location that is marked with a "1", it will usually be correct to estimate a non-zero percentage of silicone within the relative substance composition (RSC).

In some embodiments, refinements, or variants of embodiments, the at least one piece of patient information data (PPID) includes at least one (e.g., all) of the following: at least one a piece of information indicating the sex of the patient (e.g., a particular binary numerical entry of an input vector may show "0" for biological female and "1" for biological male or vice versa); at least one piece of information indicating at least one size or sizing of the patient (e.g., a particular numerical entry of an input vector may indicate the size of the size of the patient in a given unit (centimeter, inch, . . . ) or a clothing sizing for at least one body part), and multiple entries of an input vector may indicate different sizes or sizings for different body parts; at least one piece of information indicating a weight of the patient (e.g., a particular numerical entry of an input vector may indicate the weight of the patient weight in a given unit (kilograms, pounds, . . . ); at least one piece of information indicating the age of the patient (e.g., a particular numerical entry of an input vector may indicate the age of the patient in a given unit (years, months, . . . ) or their birth date); at least one piece of information indicating information about implants in the body of the patient (e.g., as has been described in the foregoing, an input vector may include an entry for each of a predefined set of body regions, where each entry shows a "0" if no such silicone implant is present in the corresponding location and shows a "1" if there is a silicone implant present therein). For additional substances or types of implants (e.g., pacemakers, surgical steel replacements), additional entries of the input vector may be provided (e.g., again one entry per body region per substance/type of implant).

In some embodiments, refinements, or variants of embodiments, the at least one PFID includes at least one (e.g., all) of the following: at least one piece of information indicating a field-of-view position (e.g., one entry of an input vector may indicate an x-value, another entry a y-value, and a third entry a z-value in a given coordinate system); at least one piece of information indicating a field-of-view size; and/or at least one piece of information indicating a field-of-view rotation.

In some embodiments, refinements, or variants of embodiments, the input interface is further configured to receive at least one piece of information indicating a positioning of the patient or at least one PPPI, and the trained MLA is further configured and trained to receive the at least one PPPI as part of an input, and to generate the at least one output signal also based on the at least one PPPI. The patient positioning may, for example, indicate how the body of the patient is positioned relative to the B0 homogeneity area and/or indicate a table position of a table on which the patient rests. A particular organ to be imaged may be easily selected by choosing a combination of the field of view and the patient positioning.

The PPPI may, for example, be a particular discrete numerical entry of an input vector that indicates a number of pre-defined positions, or may include a plurality of values indicating an absolute or relative patient positioning.

In some embodiments, refinements, or variants of embodiments, the machine learning algorithm (MLA) is a feed-forward artificial neural network (ANN). These types of artificial neural networks (ANN) are well suited for the present task. In one embodiment, the feed-forward ANN includes an input layer with at least one input node for each of the pieces of information in the at least one PPID and/or at least one input node for each of the pieces of information in the at least one PFID.

In some embodiments, refinements, or variants of embodiments, the feed-forward ANN includes an output layer with at least two output nodes (e.g., at least or exactly three output nodes) for generating the at least one output signal, where each output node outputs a signal (e.g., a sub-signal) indicating an estimate for the percentage of a particular substance within the SMR. Two output nodes may indicate estimates for the percentages of water and fat; three output nodes may indicate estimates for the percentages of water, fat, and silicone.

In some embodiments, refinements, or variants of embodiments, the feed-forward ANN includes between two and ten hidden layers with each in the range of from 32 to 5096 (both included) nodes or artificial neurons (e.g., in the range from 128 to 2048 (both included), or in the range from 256 to 1024 (both included)). Feed-forward ANNs with these dimensions of layers may be well suited for the task at hand.

In some embodiments, refinements, or variants of embodiments, after each of the hidden layers, a drop-out function is applied, where the dropout rate of each drop-out function is in the range of from 10% to 90% (both included) or in the range from 20% to 50% (both included).

In some embodiments, the dropout rate is different in at least two of the applied drop-out functions. In some embodiments, the feed-forward ANN may include three hidden layers with (e.g., from layers closer to the input layer to layers closer to the output layer) 1024, 1024, and 256 neurons, respectively, where dropout functions with dropout rates of 20%, 50%, and 40% are applied after every layer, respectively. In other words, after an input layer, a first hidden layer with 1024 nodes, a dropout function with 20% dropout rate, a second hidden layer with 1024 nodes, thereafter a dropout function with 50% dropout rate, then a third hidden layer with 256 nodes, thereafter a dropout function with 40% dropout rate, and then the output layer follow.

According to a second aspect, the present embodiments provide a method for estimating a relative substance composition (RSC) of a portion of a body of a patient in a field of view for a medical image to be taken from the patient in a medical imaging scan. The method includes receiving at least one piece of patient information data (PPID), receiving at least one piece of field-of-view information data (PFID), and inputting the received at least one PPID and the received at least one PFID into a trained machine learning algorithm (MLA). The trained MLA is trained to receive the at least one PPID and the at least one PFID as an input and to generate as an output at least one output signal indicating a relative substance composition (RSC) of the body of the patient for the medical image based on the at least one PPID and the at least one PFID. At least the at least one output signal is output.

Thus, a method for using the system according to any embodiment of the first aspect of the present invention is also provided.

In some embodiments, refinements, or variants of embodiments, the at least one output signal is used in a method for determining a water resonance setting frequency for a magnetic resonance imaging (MRI) scan and/or is used in a shimming method for an MRI device (e.g., in a multi-echo-B0 shimming method). In this case, the present embodiments also provide a method for determining a water resonance setting frequency for a magnetic resonance imaging (MRI) scan, as well as a shimming method for an MRI device.

In some embodiments, refinements, or variants of embodiments, the method includes receiving at least one piece of information indicating a positioning of the patient (e.g., at least one piece of patient positioning information (PPPI)). The at least one received PPPI is input into the trained MLA that is further configured and trained to receive the at least one piece of patient positioning information (PPPI) as part of an input, and to generate the at least one output signal also based on the at least one piece of patient positioning information (PPPI).

According to a third aspect, a method for training a machine learning algorithm (MLA) for use in the system according to any embodiment of the first aspect or for use in the method according to any embodiment of the second aspect is provided. The method includes providing training samples, each including a set of input parameters including at least one piece of patient information data (PPID) and at least one piece of field-of-view information data (PFID) in accordance with pieces of information that the MLA is configured to receive. Each of the training samples is labeled with a corresponding relative substance composition (RSC), and the MLA is trained with supervised learning using the provided training samples.

Training the MLA may include training the MLA by inputting the provided training samples into the MLA and by adjusting trainable or learnable parameters of the MLA to minimize a loss function. The loss function penalizes differences between the RSC indicated by the at least one output signal based on each training sample and the corresponding RSC, with which the corresponding set has been labeled.

According to a fourth aspect, a method for providing training samples for use in the method according to any embodiment of the third aspect of the present embodiments is provided. The method includes providing at least one family member of a virtual family. Each family member includes a plurality of voxels for which the individual relative substance composition (RSC) is known. The method also includes virtually positioning each of the at least one family member in a plurality of positions and with a plurality of fields-of-view with regard to a medical imaging scan, and optionally additionally with a plurality of table positions. The method includes determining, for each position and field-of-view for each family member of the virtual family, a total relative substance composition (RSC) for the respective field of view based on the individual RSCs of the voxels of the respective family member in the respective field of view at the respective position. The method also includes generating sets of input parameters including at least one piece of patient information data (PPID) and at least one piece of field-of-view information data (PFID) based on the at least one family member, the plurality of positions, and the plurality of fields-of-view. The method also includes labeling the generated sets with the corresponding determined total relative substance composition (RSC) to generate training samples.

In this way, a sufficiently large number of training samples may be easily generated.

According to a fifth aspect of the present embodiments, a computer program product including executable program code configured to, when executed by a computing device, perform the method according to any embodiment of the second aspect and/or the third aspect and/or the fourth aspect of the present embodiments is provided.

According to a sixth aspect of the present embodiments, a non-transitory, computer-readable data storage medium is provided. The non-transitory, computer-readable data storage medium includes program code configured to, when executed by a computing device, perform the method according to any embodiment of the second aspect and/or the third aspect and/or the fourth aspect of the present embodiments. Such a data storage medium may be, for example, a USB stick, a CD ROM, a DVD ROM, a Blue-Ray Disc, a hard drive, a solid state drive, and/or the like.

According to a seventh aspect of the present embodiments, a data stream that includes program code or is configured to generate program code, configured to, when executed by a computing device, perform the method according to any embodiment of the second aspect and/or the third aspect and/or the fourth aspect is provided. The data stream may, for example, be provided by a server and be downloaded by a client or a user terminal or by a personal computer or a laptop.

Additional advantageous variants, refinements, embodiments and, aspects of the invention will become more obvious in connection with the following description with reference to the drawings.

BRIEF DESCRIPTION OF THE DRAWINGS

The accompanying drawings are included to provide a further understanding of the present embodiments and are incorporated in and constitute a part of the specification. The drawings illustrate the embodiments and, together with the description, serve to illustrate the principles of the present embodiments. Other embodiments and many of the intended advantages of the present embodiments will be readily appreciated as the other embodiments and the intended advantages become better understood by reference to the following detailed description. Like reference numerals designate corresponding similar parts.

The numbering of method acts is intended to facilitate understanding and should not be construed, unless explicitly stated otherwise, or implicitly clear, to provide that the designated acts have to be performed according to the numbering of reference signs. For example, a number or even all of the method acts may be performed simultaneously, in an overlapping way or sequentially.

Although specific embodiments have been illustrated and described herein, it will be appreciated by those of ordinary skill in the art that the variety of alternate and/or equivalent implementations may be substituted for the specific embodiments shown and described without departing from the scope of the present invention. Generally, this application is intended to cover any adaptations or variations of the specific embodiments discussed herein.

DETAILED DESCRIPTION

Figure 1:
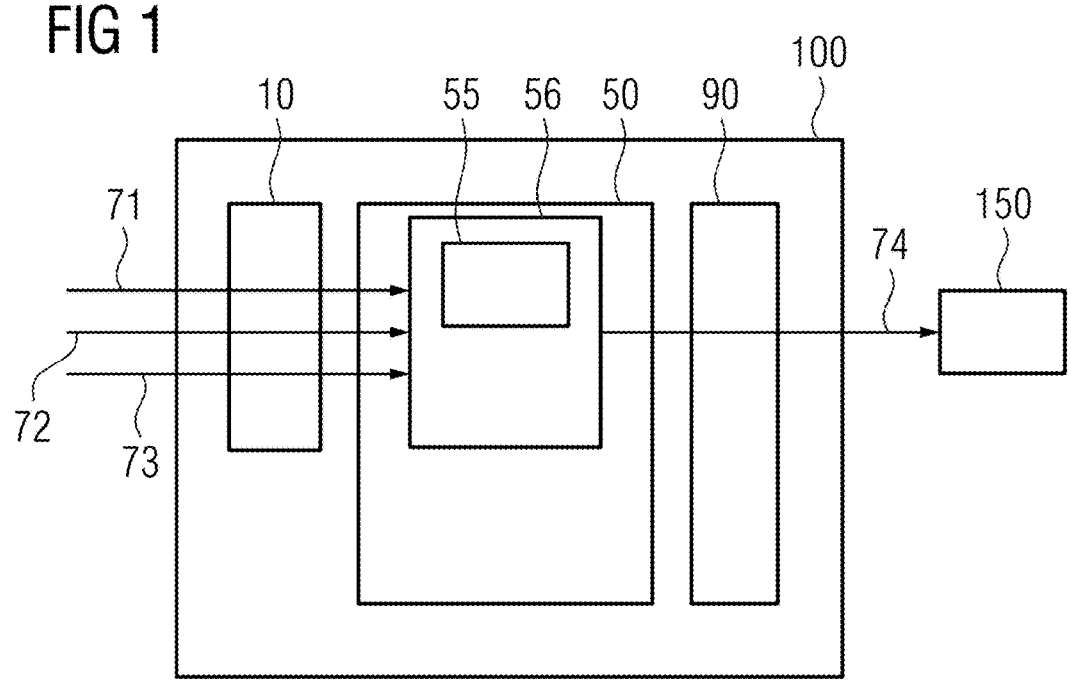
FIG. 1 shows a schematic block diagram illustrating a system according to an embodiment of a first aspect.

FIG. 1 shows a schematic block diagram illustrating a system 100 according to a first aspect of an embodiment. Thus, FIG. 1 shows a schematic block diagram of one embodiment of a system 100 for estimating a relative substance composition (RSC) of a portion of a body of a patient in a field of view for a medical image to be taken from the patient in a medical imaging scan.

The system 100 includes an input interface 10 for receiving at least one piece of patient information data (PPID) 71, for receiving at least one piece of field-of-view information data (PFID) 72, and for receiving at least one piece of patient positioning information (PPPI) 73.

The at least one PPID 71 may include any or all of the pieces of information that have been discussed in the foregoing. The at least one PFID 72 may include any or all of the pieces of information that have been discussed in the foregoing. The at least one PPPI 73 may, for example, be at least one piece of information indicating a positioning of the patient and/or indicating a table position of a table on which the patient rests.

The system 100 also includes a computing device 50 configured to implement a trained machine learning algorithm (MLA) 55. The computing device 50 may include a dedicated MLA module 56 configured to implement the trained MLA 55. The MLA module 56 may, for example, be realized as software run by the computing device 50, where the software may be stored in a non-transitory data storage of the computing device 50 and may be run in a working memory of the computing device 50.

The trained MLA 55 is trained to receive the PPID 71, the PFID 72 and the PPPI 73 received by the input interface 10 as an input and to generate, as an output, based thereon, at least one output signal 74. The at least one output signal 74 indicates an RSC of a portion of the body of the patient for the medical image (e.g., a relative substance ratio between water, fat, and silicone).

The system 100 further includes an output interface 90 for outputting the generated at least one output signal 74. The generated at least one output signal 74 may be output, for example, to an external database for storing therein, or to any further device that makes use of the output signal 74 (e.g., of the information about the relative substance composition (RSC)).

As is described elsewhere herein, the generated at least one output signal 74 may also be transmitted to a magnetic resonance imaging (MRI) device 150.

The MRI device 150 may be part of the system 100. For example, the input interface 10, the computing device 50, and the output interface 90 may be integrated into a housing of the device 150.

The MRI device 150 may be configured to perform a method for determining and setting a water resonance frequency setting based on the at least one output signal 74. For example, the MRI device 150 may be configured to perform a pre-scan, obtain thereby a resonance frequency spectrum (RFS), and to then determine, based on the RSF and on the RSC indicated by the at least one output signal 3, an optimal water resonance frequency setting or analogue. The MRI device 150 is also configured to set this optimal water resonance frequency setting for the MRI device 150.

Alternatively or additionally, the MRI device 150 may be configured to perform a shimming method based on the at least one output signal 74 (e.g., based on the relative substance composition (RSC) indicated thereby).

In the following, the case in which the machine learning algorithm (MLA) 55 is an artificial neural network (ANN) (e.g., a feed-forward artificial neural network) is described.

The ANN includes an input layer with at least one input node for each PPID 71, with at least one input node for each PFID 72, and with at least one input node for each PPPI 73. For example, pieces of information of PPID 71, PFID 72, or PPPI 73 that indicate one of a plurality of classes may be realized as a one-hot vector, or as a single value indicating the class. For example, the PPID 71 regarding the sex of a patient may be realized as a one-hot vector, where [1,0] indicates female and [0,1] indicates male; alternatively, the PPID 71 regarding the sex of the patient may be realized as a single value, where 0 indicates male, 1 indicates female, and 2 indicates diverse/neutral.

Thus, the input layer of the ANN may, as an example, include nodes for the following input information.

Nodes for PPID 71, with, for example, possible values or dimensions for values in square brackets are provided:
1x sex [0, 1, 2]
1x height [ . . . m]
1x weight [ . . . kg]
1x age [ . . . years]
1x silicone implant in left breast [0, 1]
1x silicone implant in right breast [0, 1]
Nx silicone implant in . . . [N possible body parts/sections where silicone implants are possible, leading to N additional input nodes]
Nodes for PFID 72 with dimensions of values in square brackets:
1x field of view position in X direction [ . . . m]
1x field of view position in Y direction [ . . . m]
1x field of view position in Z direction [ . . . m]
1x field of view size in X direction [ . . . m]
1x field of view size in Y direction [ . . . m]
1x field of view size in Z direction [ . . . m]
1x field of view rotation [ . . . °]
Nodes for PPPI 73, with dimensions of values in square brackets:
1x patient positioning [0, 1, 2, 3, 4, 5, 6, 7, 8, 9, . . . ]
1x table position in Z direction [ . . . m]

Thus, in this example, the input layer of the feed-forwards ANN includes 14+N input nodes.

The ANN further includes an output layer with one node for each of the substances to be determined in the RSC. For example, in the case of water, fat, and silicone, the output layer includes three output nodes. The redundancy provided by providing explicit values for all three substances (e.g., rather than providing two, and calculating the third) is intended and may be used for a plausibility analysis of the results.

Between the input layer and the output layer, the ANN includes at least one hidden layer. In one embodiment, the feed-forward ANN may include three hidden layers with (e.g., from layers closer to the input layer to layers closer to the output layer) 1024, 1024, and 256 neurons, respectively, where dropout functions with dropout rates of 20%, 50%, and 40% being applied after every layer, respectively. In other words, after the input layer, a first hidden layer with 1024 nodes, thereafter a dropout function with 20% drop-out rate, then a second hidden layer with 1024 nodes, thereafter a dropout function with 50% dropout rate, then a third hidden layer with 256 nodes, thereafter a dropout function with 40% dropout rate, and then the output layer follow.

Figure 2:
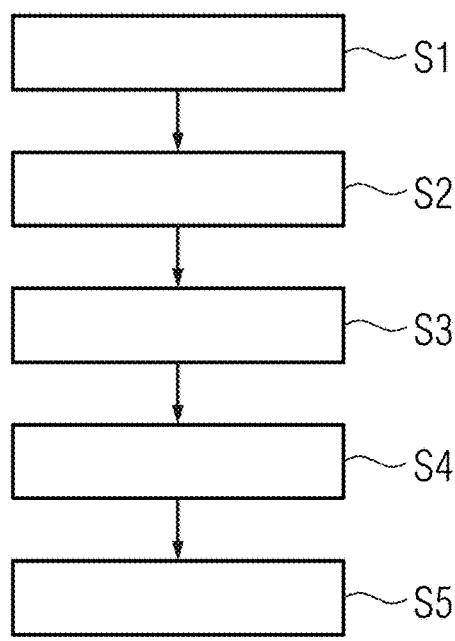
FIG. 2 shows a schematic flow diagram illustrating a computer-implemented method according to an embodiment of a second aspect.

FIG. 2 shows a schematic flow diagram schematically illustrating one embodiment of a computer-implemented method for estimating an RSC of a portion of a body of a patient in a field of view for a medical image to be taken from the patient in a medical imaging scan.

The method of FIG. 2 may be performed, for example, with the system according to any embodiment of the first aspect of the present embodiments (e.g., with the system as has been described with respect to FIG. 1). Thus, the method of FIG. 2 may be modified according to any modifications or variants of the system according to any embodiment of the first aspect and vice versa. Any or all of the method acts described in the following may also be performed simultaneously or essentially simultaneously.

In act S1, at least one PPID 71 is received (e.g., via an input interface 10 as has been described in the foregoing).

For example, any or all of the following may be received as PPID 71: a particular binary numerical entry of an input vector may show "0" for biological female and "1" for biological male or vice versa; at least one piece of information indicating at least one size or sizing of the patient (e.g., a particular numerical entry of an input vector may indicate the size of the patient in a given unit (centimeter, inch, . . . ) or a clothing sizing for at least one body part), and multiple entries of an input vector may indicate different sizes or sizings for different body parts; at least one piece of information indicating a weight of the patient (e.g., a particular numerical entry of an input vector may indicate the weight of the patient in a given unit (kilograms, pounds, . . . )); at least one piece of information indicating the age of the patient (e.g., a particular numerical entry of an input vector may indicate the age of the patient in a given unit (years, months, . . . )); and at least one piece of information indicating information about implants in the body of the patient (e.g., as has been described in the foregoing, an input vector may include an entry for each of a predefined set of body regions, where each entry shows a "0" if no such silicone implant is present in the corresponding location and shows a "1" if there is a silicone implant present therein). For additional substances or types of implants (e.g., pacemakers, surgical steel replacements), additional entries of the input vector may be provided (e.g., one entry per body region per substance/type of implant).

In act S2, at least one PFID 72 is received (e.g., via an input interface 10 as has been described in the foregoing).

For example, any or all of the following may be received as PFID 72: at least one piece of information indicating a field-of-view position (e.g., one entry of an input vector may indicate an x-value, another entry a y-value, and a third entry a z-value in a given coordinate system); at least one piece of information indicating a field-of-view size; and/or at least one piece of information indicating a field-of-view rotation.

In an optional act S3, at least one PPPI 73 is received (e.g., at least one piece of information indicating a positioning of the patient and/or indicating a table position of a table on which the patient rests).

In act S4, the received at least one PPID 71 and the received at least one PFID 72 (e.g., and optionally the at least one PPPI 73) are input into a trained MLA 55 (e.g., into a trained feed-forward ANN). The ANN is configured and trained to receive the at least one PPID 71 and the at least one PFID 72 (and optionally the at least one PPPI 73) as an input and to generate as an output at least one output signal 74 indicating an RSC of the body of the patient for the medical image based on the at least one PPID 71 and the at least one PFID 72 (e.g., and optionally the at least one PPPI 73).

In act S5, at least the at least one output signal 74 is output (e.g., via the output interface 90 as has been described in the foregoing).

In optional additional acts, the output signal 74 may be used in a method for determining a water resonance setting frequency for an MRI scan and/or used in a shimming method for an MRI device 150 (e.g., in a multi-echo-B0 shimming method).

Figure 3:
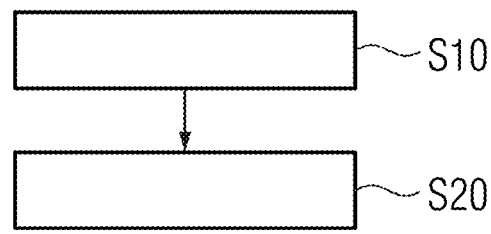
FIG. 3 shows a schematic flow diagram illustrating a computer-implemented method according to an embodiment of a third aspect.

FIG. 3 shows a flow diagram schematically illustrating one embodiment of a computer-implemented method for training an MLA 55 (e.g., an ANN) for use in a method or a system according to any embodiment of the first aspect or the second aspect. For example, the method illustrated with respect to FIG. 3 may be used for training an MLA 55 for use in a system 100 of FIG. 1 and/or for use with the method described with respect to FIG. 2.

In act S10, training samples (e.g., labeled training samples) are provided, each including a set of input parameters including at least one PPID 71 and at least one PFID 72 (e.g., and optionally at least one PPPI 73) in accordance with pieces of information that the MLA 55 is configured and trained to receive, and each labeled with a corresponding RSC.

In act S20, the MLA 55 is trained with supervised learning using the provided training samples (e.g., provided labeled training samples), for example, using standard gradient propagation, known optimizers such as the ADAM optimizer, and/or the like.

Figure 4:
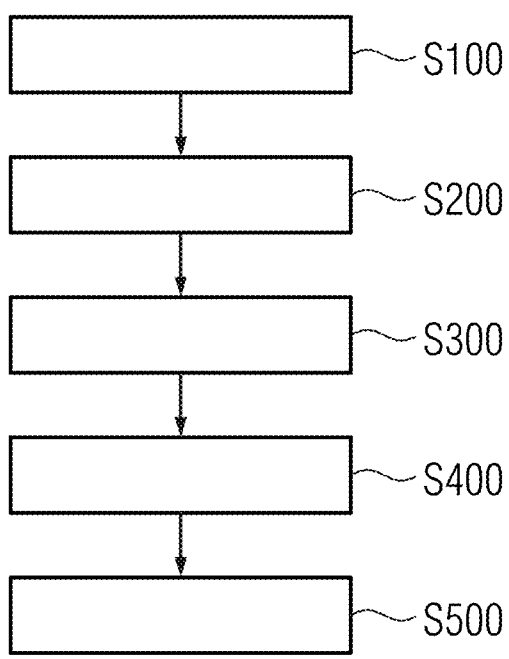
FIG. 4 shows a schematic flow diagram illustrating a computer-implemented method according to an embodiment of a fourth aspect.

FIG. 4 shows a schematic flow diagram illustrating a method according to an embodiment of the fourth aspect of the present embodiments (e.g., a method for providing training samples for use in the method according to any embodiment of the third aspect of the present embodiments, such as for use in the method of FIG. 3).

In act S100, at least one family member of a virtual family is provided, where each family member of the virtual family includes a plurality of voxels for which the individual (RSC) is known.

In act S200, each family member of the at least one family member is virtually positioned in a plurality of positions with a plurality of fields-of-view with regard to a medical imaging scan, and optionally also with a plurality of table positions.

In act S300, for each position and field-of-view (e.g., and optionally for each table position of the plurality of table positions) for each family member of the virtual family, a total RSC is determined for the respective field of view based on the individual RSCs of the voxels of the respective family member in the respective field of view at the respective position (e.g., and optionally with the respective table position).

In act S400, sets of input parameters that include at least one PPID 71 and at least one PFID 72 (e.g., and optionally also at least one PPPI 73) are generated based on the at least one family member, the respective position out of the plurality of positions and the respective field of view out of the plurality of fields-of-view (e.g., and optionally also on the respective table position out of the plurality of table positions).

In act S500, the generated sets are labeled with the corresponding determined total RSC to generate training samples.

Figure 5:
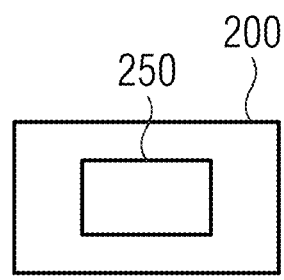
FIG. 5 shows a schematic block diagram illustrating a computer program product according to an embodiment of a fifth aspect.

FIG. 5 shows a schematic block diagram illustrating a computer program product 200 according to an embodiment of the third aspect of the present embodiments. The computer program product 200 includes executable program code 250 configured to, when executed by a computing device (e.g., computing device 50 of system 100), to perform the method according to FIG. 2. Alternatively or additionally, the computer program product 200 may include executable program code 250 configured to, when executed by a computing device (e.g., computing device 50 of system 100), to perform the method according to FIG. 3. Alternatively or additionally, the computer program product 200 may include executable program code 250 configured to, when executed by a computing device (e.g., computing device 50 of system 100), to perform the method according to FIG. 4.

Figure 6:
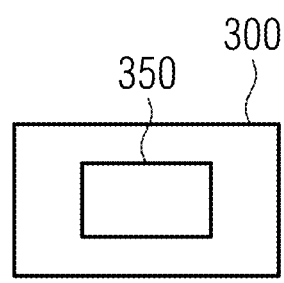
FIG. 6 shows a schematic block diagram illustrating a data storage medium according to an embodiment of a sixth aspect.
Figure 7:
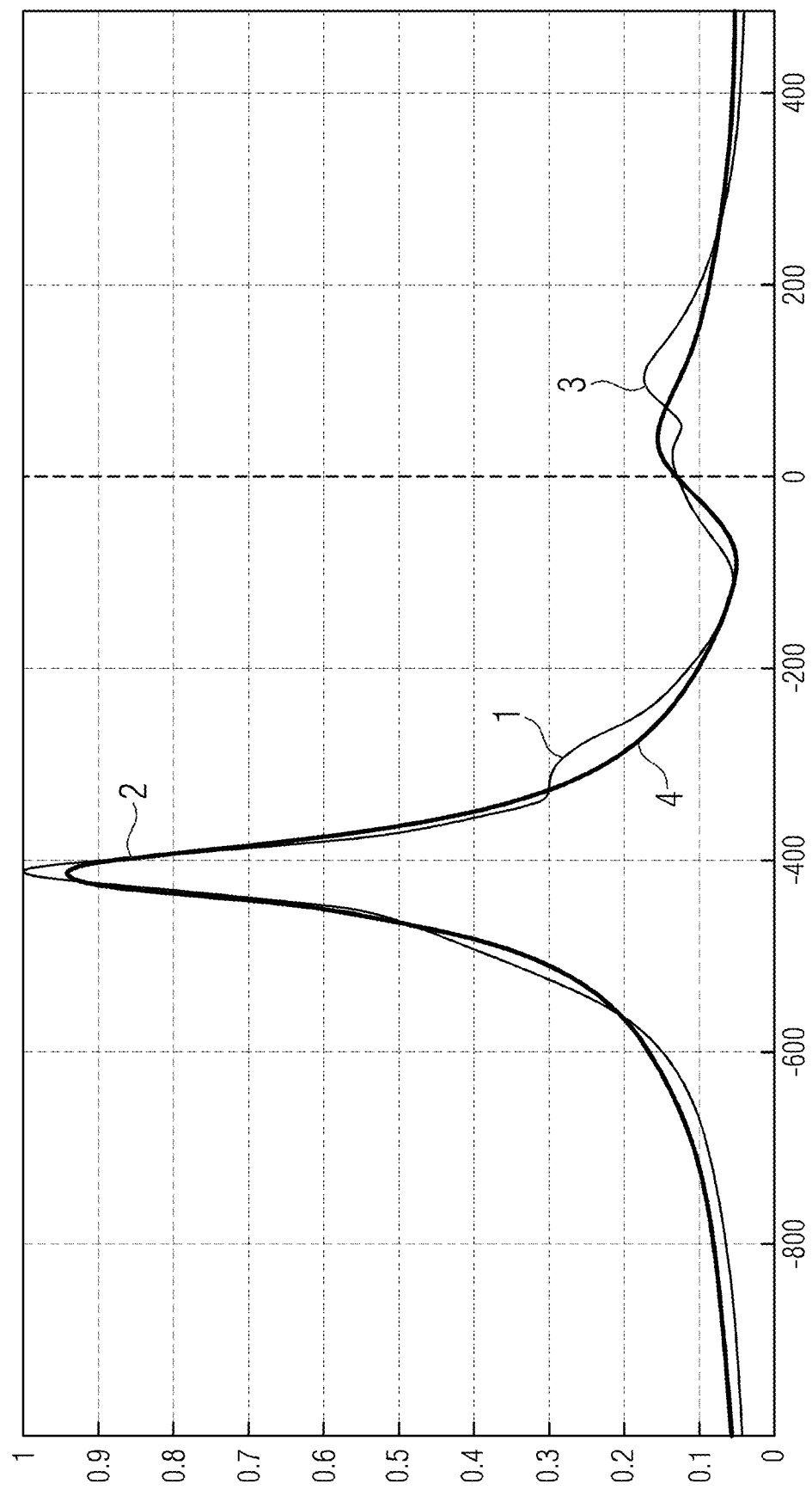
FIG. 7 and FIG. 8 illustrate typical resonance frequency spectra and the associated issues.
Figure 8:
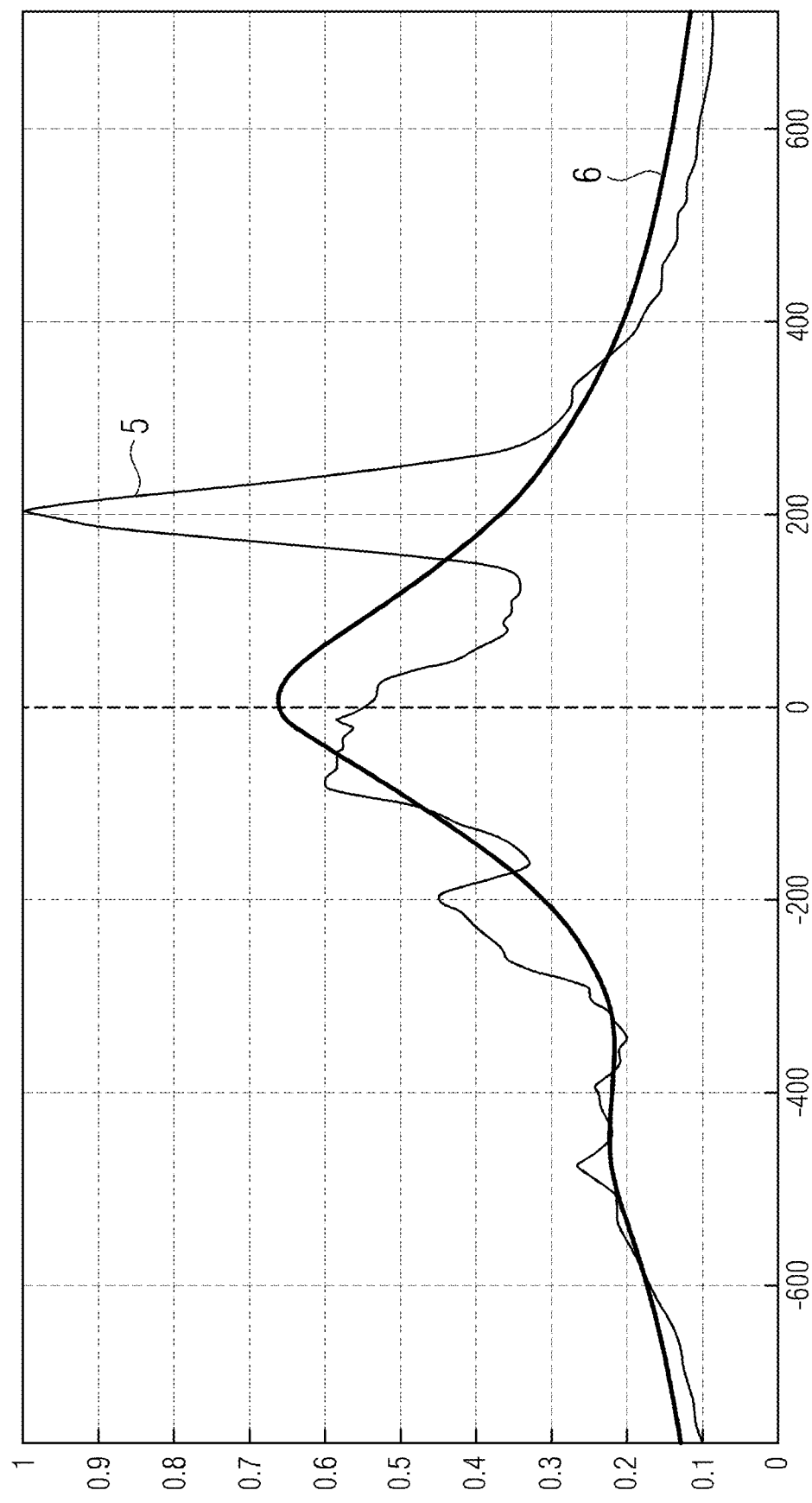

FIG. 6 shows a schematic block diagram illustrating one embodiment of a non-transitory, computer-readable data storage medium 300 including executable program code 350 configured to, when executed by a computing device (e.g., computing device 50 of system 100), to perform the method according to FIG. 2. Alternatively or additionally, the data storage medium 300 may include executable program code 350 configured to, when executed by a computing device (e.g., computing device 50 of system 100), to perform the method according to FIG. 3. Alternatively or additionally, the data storage medium 300 may include executable program code 350 configured to, when executed by a computing device (e.g., computing device 50 of system 100), to perform the method according to FIG. 4.

In the foregoing detailed description, various features are grouped together in the examples with the purpose of streamlining the disclosure. It is to be understood that the above description is intended to be illustrative and not restrictive. The description is intended to cover all alternatives, modifications and equivalence. Many other examples will be apparent to one skilled in the art upon reviewing the above specification, taking into account the various variations, modifications and options as described or suggested in the foregoing.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A system for estimating a relative substance composition (RSC) of a portion of a body of a patient in a field of view for a medical image to be taken from the patient in a medical imaging scan, the system comprising:
   an input interface configured to:
      receive at least one piece of patient information data (PPID); and
      receive at least one piece of field-of-view information data (PFID), wherein the PFID is indicative of the field of view with which the medical image is to be taken of the patient;
   a computing device configured to implement a trained machine learning algorithm,
   wherein the trained MLA is configured and trained to:
      receive the at least one PPID and the at least one PFID received by the input interface as input; and
      generate as output at least one output signal indicating an RSC of a portion of the body of the patient for the medical image based on the at least one PPID and the at least one PFID; and
   an output interface configured to output at least the at least one output signal.

2. A computer-implemented method for estimating a relative substance composition (RSC) of a portion of a body of a patient in a field of view for a medical image to be taken from the patient in a medical imaging scan, the computer-implemented method comprising:
   receiving at least one piece of patient information data (PPID);
   receiving at least one piece of field-of-view information data (PFID), wherein the PFID is indicative of the field of view with which the medical image is to be taken of the patient;
   inputting the received at least one PPID and the received at least one PFID into a trained machine learning algorithm (MLA), wherein the trained MLA is configured and trained to receive the at least one PPID and the at least one PFID as an input and to generate as an output at least one output signal indicating a relative substance composition (RSC) of the body of the patient for the medical image based on the at least one PPID and the at least one PFID; and
   outputting at least the at least one output signal.

3. A computer-implemented method for training a machine learning algorithm (MLA) for use in a system for estimating a relative substance composition (RSC) of a portion of a body of a patient in a field of view for a medical image to be taken from the patient in a medical imaging scan, the system comprising an input interface configured to receive at least one piece of patient information data (PPID) and receive at least one piece of field-of-view information data (PFID), wherein the PFID is indicative of the field of view with which the medical image is to be taken of the patient, a computing device configured to implement a trained machine learning algorithm, wherein the trained MLA is configured and trained to receive the at least one PPID and the at least one PFID received by the input interface as input, and generate as output at least one output signal indicating an RSC of a portion of the body of the patient for the medical image based on the at least one PPID and the at least one PFID, and an output interface configured to output at least the at least one output signal, the computer-implemented method comprising:
   providing training samples, each of the training samples comprising a set of input parameters comprising one or more PPID and one or more PFID in accordance with pieces of information that the MLA is configured to receive, and each of the training samples being labelled with a corresponding RSC; and
   training the MLA with supervised learning using the provided training samples.

4. A method for providing training data for use in a computer-implemented method for training a machine learning algorithm (MLA), the method comprising:
   providing at least one family member of a virtual family, wherein each family member of the at least one family member comprises a plurality of voxels for which an individual relative substance composition (RSC) is known;
   virtually positioning each family member of the at least one family member in a plurality of positions and with a plurality of fields-of-view with regard to a medical imaging scan;
   determining, for each position of the plurality of positions and field-of-view of the plurality of fields-of-view for each family member of the at least one family member of the virtual family, a total RSC for a respective field of view based on the individual RSCs of the voxels of the family member in the respectively field of view at the respective position;
   generating sets of input parameters comprising at least one PPID and at least one PFID based on the at least one family member, the plurality of positions, and the plurality of fields-of-view;
   labelling the generated sets of input parameters with the corresponding determined total RSC, such that training samples are generated.

5. In a non-transitory computer-readable storage medium that stores instructions executable by one or more processors to estimate a relative substance composition (RSC) of a portion of a body of a patient in a field of view for a medical image to be taken from the patient in a medical imaging scan, the instructions comprising:
   receiving at least one piece of patient information data (PPID);

receiving at least one piece of field-of-view information data (PFID), wherein the PFID is indicative of the field of view with which the medical image is to be taken of the patient;

inputting the received at least one PPID and the received at least one PFID into a trained machine learning algorithm (MLA), wherein the trained MLA is configured and trained to receive the at least one PPID and the at least one PFID as an input and to generate as an output at least one output signal indicating a relative substance composition (RSC) of the body of the patient for the medical image based on the at least one PPID and the at least one PFID; and outputting at least the at least one output signal.

6. The system of claim 1, wherein the RSC comprises or consists of a ratio between water, fat, and silicone.

7. The system of claim 1, wherein the at least one PPID comprises at least one piece of information indicating sex of the patient, at least one piece of information indicating at least one size or sizing of the patient, at least one piece of information indicating a weight of the patient, at least one piece of information indicating an age of the patient, at least one piece of information indicating information about implants in the body of the patient, or any combination thereof.

8. The system of claim 7, wherein the at least one PPID comprises, for each of a plurality of predefined body regions, a piece of information about whether or not the body region of the patient comprises a silicone implant.

9. The system of claim 1, wherein the at least one PFID comprises at least one piece of information indicating a field-of-view position, at least one piece of information indicating a field-of-view size, at least one piece of information indicating a field-of-view rotation, or any combination thereof.

10. The system of claim 1, wherein the input interface is further configured to receive at least one piece of patient positioning information (PPPI), and wherein the MLA is configured and trained to also receive the at least one PPPI as part of input and to generate the output signal based in addition also on the PPPI.

11. The system of claim 1, wherein the MLA is a feed-forward artificial neural network (ANN) that comprises an input layer with at least one input node for each of the pieces of information in the at least one PPID, at least one input node for each of the pieces of information in the at least one PFID, or a combination thereof.

12. The system of claim 6, wherein the input interface is further configured to receive at least one piece of patient positioning information (PPPI), wherein the MLA is configured and trained to also receive the at least one PPPI as part of input and to generate the output signal based in addition also on the PPPI, wherein a feed-forward artificial neural network (ANN) comprises an output layer with at least three output nodes for generating the output signal, and wherein each output node of the at least three output nodes outputs a signal indicating an estimate for a percentage of a particular substance within a signal-to-noise ratio.

13. The system of claim 10, wherein a feed-forward artificial neural network (ANN) comprises between two and ten hidden layers with each between 32 and 5096 nodes, wherein after each of the hidden layers, a drop-out function is applied, and wherein a drop-out rate of each drop-out function is between 10% and 90%.

14. The system of claim 9, wherein the at least one piece of information indicating a field-of-view position comprises a first entry of an input vector indicating an x-value, a second entry indicating a y-value, and a third entry indicating a z-value in a given coordinate system.

15. The method of claim 2, wherein the at least one output signal is used in a method for determining a water resonance setting frequency for a magnetic resonance imaging (MRI) scan, is used in a shimming method for an MRI device, or is used in the method for determining the water resonance setting frequency for the MRI scan and in the shimming method for the MRI device.

16. The method of claim 15, wherein the shimming method for the MRI device is a multi-echo-B0 shimming method.

* * * * *